(12) United States Patent
Ma et al.

(10) Patent No.: US 10,032,552 B2
(45) Date of Patent: Jul. 24, 2018

(54) COVER FOR TISSUE PENETRATING DEVICE WITH INTEGRATED MAGNETS AND MAGNETIC SHIELDING

(71) Applicant: Becton, Dickinson and Company, Franklin Lakes, NJ (US)

(72) Inventors: Yiping Ma, Layton, UT (US); Jonathan Karl Burkholz, Salt Lake City, UT (US); Weston Harding, Lehi, UT (US); S. Ray Isaacson, Layton, UT (US); Jeffrey C. O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/251,637

(22) Filed: Aug. 30, 2016

(65) Prior Publication Data
US 2018/0061546 A1    Mar. 1, 2018

(51) Int. Cl.
| | |
|---|---|
| *H01F 7/20* | (2006.01) |
| *H01F 13/00* | (2006.01) |
| *A61B 34/20* | (2016.01) |
| *A61B 50/30* | (2016.01) |
| *H05K 9/00* | (2006.01) |
| *A61M 5/32* | (2006.01) |

(52) U.S. Cl.
CPC .......... *H01F 13/003* (2013.01); *A61B 34/20* (2016.02); *A61B 50/3001* (2016.02); *A61M 5/3202* (2013.01); *H05K 9/0075* (2013.01); *A61B 2034/2051* (2016.02); *A61M 2205/0272* (2013.01); *A61M 2205/6054* (2013.01)

(58) Field of Classification Search
CPC .......... A61M 25/0606; A61M 25/0067; A61M 25/0023; A61M 2539/06

USPC ....................................................... 335/284
See application file for complete search history.

(56) References Cited

U.S. PATENT DOCUMENTS

| | | | | |
|---|---|---|---|---|
| 3,789,336 A | * | 1/1974 | Gordin ................. | H01F 7/0257 294/65.5 |
| 4,484,814 A | * | 11/1984 | Kawaguchi ........ | G01R 33/3815 174/15.4 |

(Continued)

FOREIGN PATENT DOCUMENTS

WO     2014072238 A1    5/2014

OTHER PUBLICATIONS

PCT International Search Report & Written Opinion in PCT/US2017/048997, dated Nov. 22, 2017, 15 pgs.

*Primary Examiner* — Shawki S Ismail
*Assistant Examiner* — Lisa Homza
(74) *Attorney, Agent, or Firm* — Servilla Whitney LLC

(57) ABSTRACT

A cover for magnetizing a shaft of a tissue-penetrating medical device is disclosed including a sleeve member having a hollow body to form a protective closure over the shaft of the tissue-penetrating medical device. The proximal end of the hollow body provides a receiving space for receiving the shaft of the tissue-penetrating medical device. One or more magnet is disposed on the sleeve member. A magnetic shield composed of one or more shielding materials associated with the cover that minimizes any effects to the clinical environment from magnetic fields generated within the cover. Medical devices and methods of magnetizing the shaft of a tissue-penetrating medical device using the cover are also disclosed.

20 Claims, 7 Drawing Sheets

(56) References Cited

U.S. PATENT DOCUMENTS

| | | | | |
|---|---|---|---|---|
| 4,813,729 A * | 3/1989 | Speckhart | ............... | B03C 1/284 |
| | | | | 294/65.5 |
| 5,471,186 A * | 11/1995 | Seo | ................... | H05K 13/0447 |
| | | | | 294/65.5 |
| 5,691,681 A * | 11/1997 | Okugawa | ................. | H02K 1/17 |
| | | | | 310/152 |
| 6,158,157 A * | 12/2000 | Hiscock | ................. | G09F 19/02 |
| | | | | 211/DIG. 1 |
| 6,310,532 B1 * | 10/2001 | Santa Cruz | ............. | H01F 13/00 |
| | | | | 335/284 |
| 6,471,273 B1 * | 10/2002 | Friedrich | ................. | B66C 1/04 |
| | | | | 294/65.5 |
| 8,226,540 B1 | 7/2012 | Chi | | |
| 9,616,214 B2 * | 4/2017 | Stout | .................... | A61M 39/10 |
| 2002/0193756 A1 | 12/2002 | Prindle | | |
| 2005/0192535 A1 * | 9/2005 | Takagi | ........... | A61M 25/0606 |
| | | | | 604/164.08 |
| 2010/0204660 A1 * | 8/2010 | McKinnon | ........ | A61M 25/0606 |
| | | | | 604/244 |
| 2013/0035646 A1 * | 2/2013 | Liversidge | .......... | A61M 5/3202 |
| | | | | 604/198 |
| 2013/0310808 A1 * | 11/2013 | Stout | .................... | A61M 39/10 |
| | | | | 604/537 |
| 2014/0128674 A1 * | 5/2014 | Wieters | .............. | A61B 1/00066 |
| | | | | 600/109 |
| 2014/0253270 A1 | 9/2014 | Nicholls | | |
| 2014/0323988 A1 * | 10/2014 | Magnani | ............ | A61M 39/1011 |
| | | | | 604/256 |
| 2015/0253401 A1 | 9/2015 | Rapoport | | |
| 2017/0100576 A1 * | 4/2017 | Stout | .................... | A61M 39/10 |

\* cited by examiner

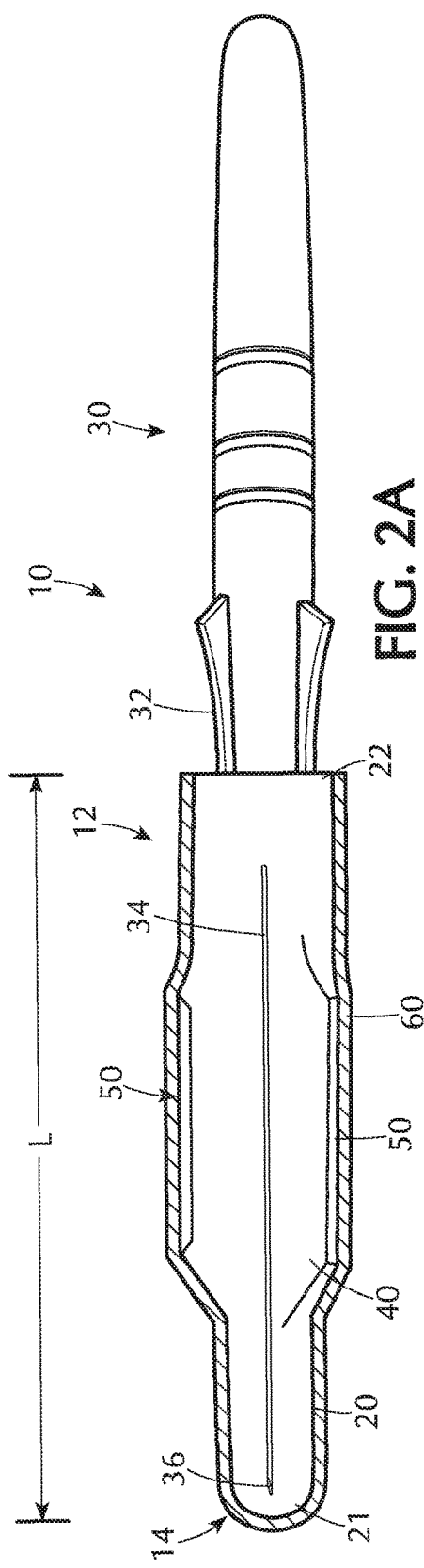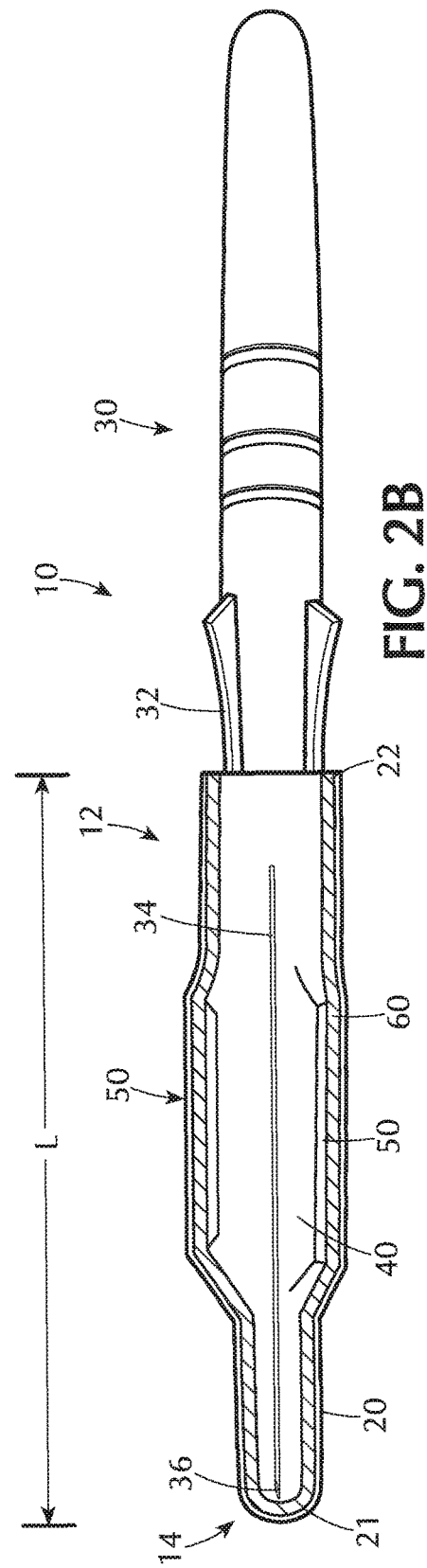

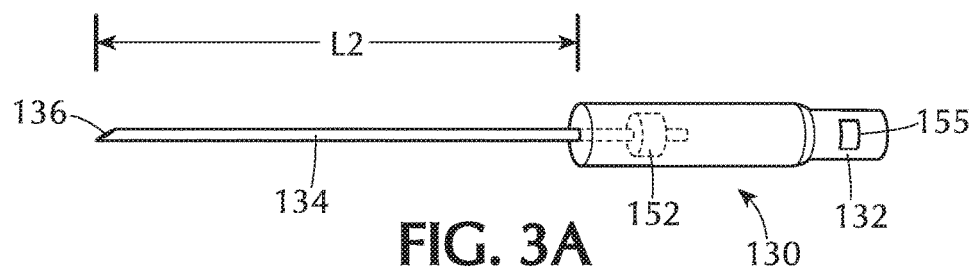
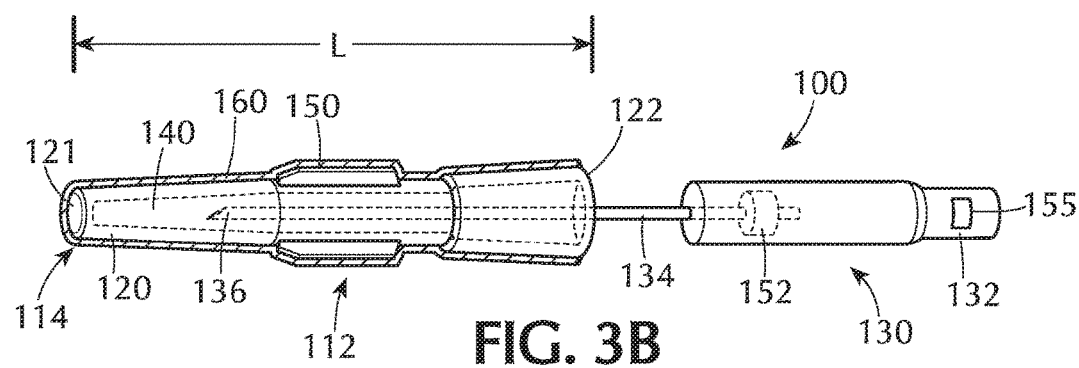
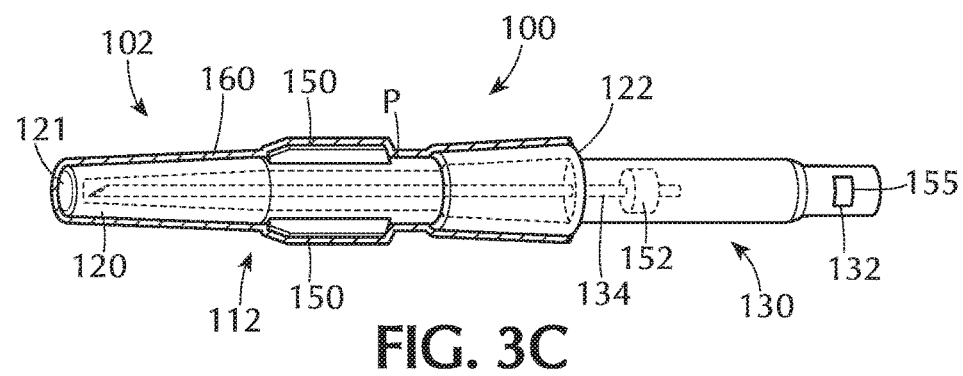

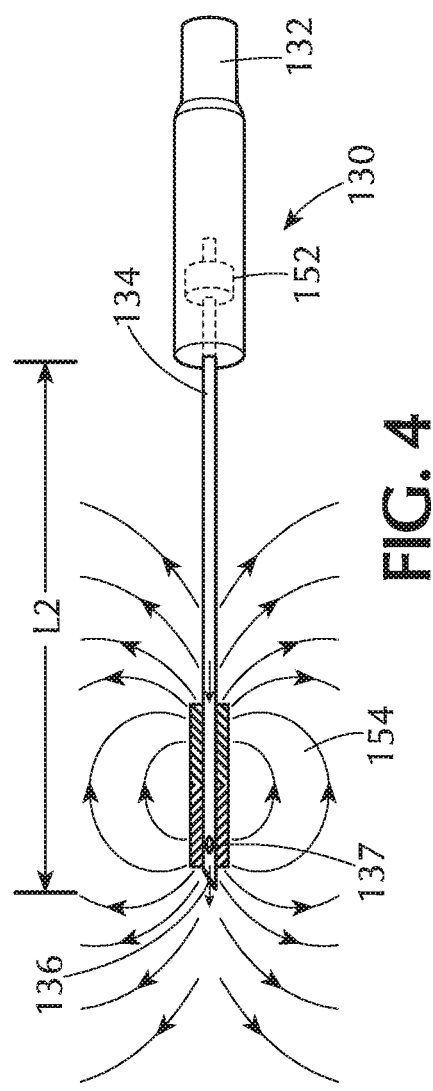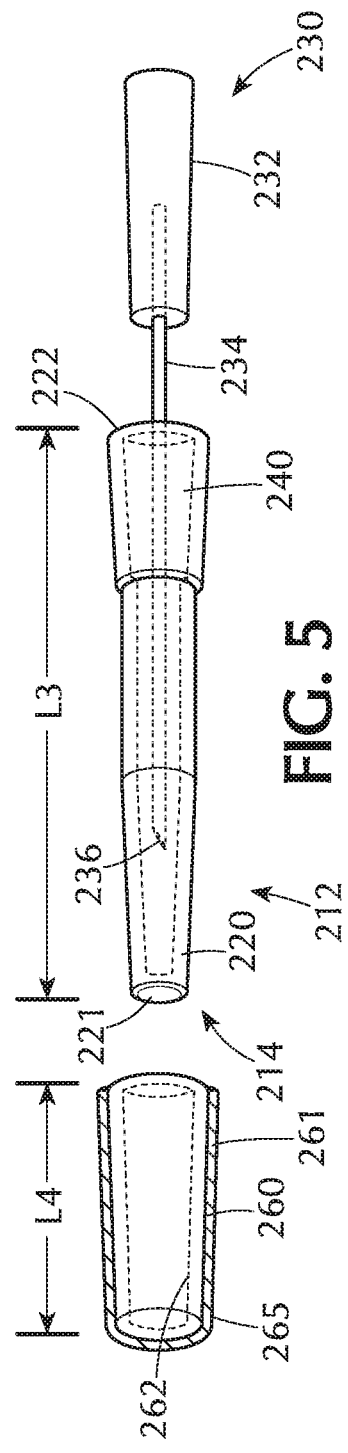
FIG. 4
FIG. 5

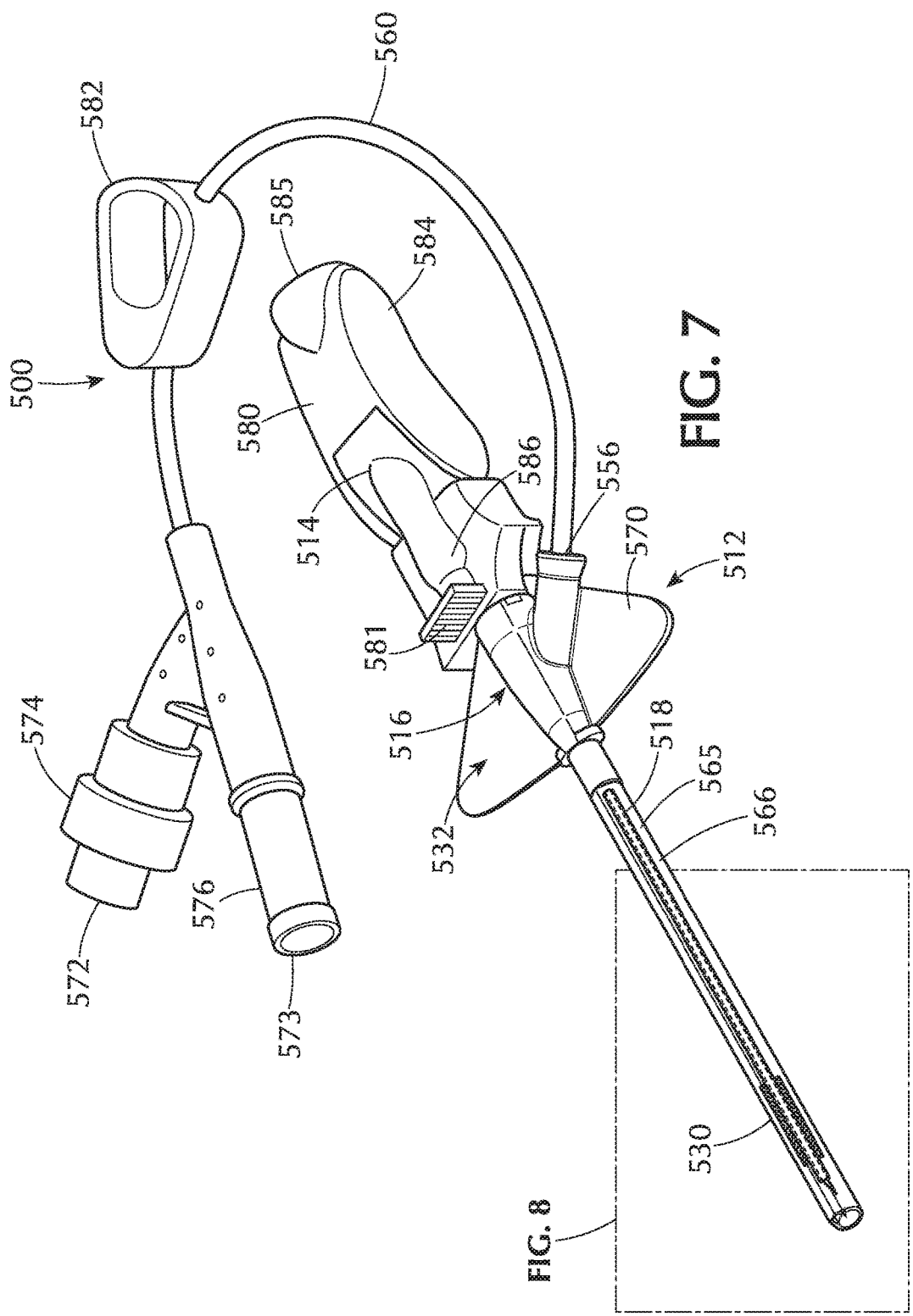

COVER FOR TISSUE PENETRATING DEVICE WITH INTEGRATED MAGNETS AND MAGNETIC SHIELDING

FIELD

Aspects of the present disclosure relate to a cover for passively magnetizing a tissue-penetrating medical device to enhance visualization during an invasive procedure when used with a procedural guidance system that utilizes magnetic sensors to locate and project the position of features on the tissue-penetrating medical device relative to targeted anatomy, while shielding the clinical environment and equipment from exposure to the magnetic field generated within the cover.

BACKGROUND

Traditionally, penetration of an invasive medical device such as a needle and catheter tubing through skin tissue to reach the vein during catheter insertion is invisible to clinicians. For this reason, clinicians must rely on their first-hand experience with needle insertion in combination with tactile sense to successfully identify the location of the vein. This may be a difficult task when attempting to access a small vein in a deep location under the skin, thereby increasing the risk of excess pain and/or injury to the patient. There are similar problems with insertion of other invasive medical devices such as guidewires, catheters, introducer needles, stylets, scalpel and guidewire with respect to the inability to precisely visualize the location of the invasive medical device.

Emerging procedural guidance systems utilize a combination of ultrasound and magnetic technologies to provide visualization of subdermal anatomy and device position in the in-plane and out-of-plane orientations. This combination of ultrasound and magnetic methods also allows for the projection or anticipation of the insertion device position relative to the patient's anatomy, and thereby improves the likelihood of successfully accessing the vascular and completing the invasive procedure. The ultra-sound and magnetic procedural guidance system technology requires that the invasive device have a sufficient magnetic field source that is maintained throughout the procedure.

In some current needle guidance systems, a magnetic field is generated just prior to insertion of the needle by magnetizing the needle by burying the metal cannula of the needle into a separate external needle magnetizer until the point of the needle hits a rubber stopping surface. FIG. 1 shows a perspective view of a currently available separate external needle magnetizer 11. As shown in FIG. 1, current practice uses an unprotected needle 13 that is placed within the separate external needle magnetizer 11 to a depth defined by the bottom of the magnetizer. The current devices for magnetizing a needle prior to insertion generally are not sterile and are not disposable.

In systems of the type shown in FIG. 1, damage to the needle can occur that is not apparent to the user that can negatively affect the insertion process. Also, the step of the user actively magnetizing the metal cannula has some limitations and inherent risks as this approach does not guarantee consistent magnetization since variability in clinician procedures such as depth of insertion, speed of process, and centering of the needle in the magnetizer will result in different degrees of magnetization. Considering the potential inconsistency of a user fully inserting the needle to the bottom of the magnetizer 11, the significant risk of damaging the needle tip, and the increased potential for contamination during this step, it would be advantageous to have a system that passively and consistently magnetizes the needle without introducing the aforementioned additional risks, such as needle tip damage and increased potential for contamination.

Thus, there is a need for a system that passively and consistently magnetizes invasive medical devices thereby reducing or eliminating risks, such as needle tip damage and needle contamination while providing magnetic shielding to minimizing any effects to the clinical environment from magnetic fields generated within the cover.

SUMMARY

An aspect of the disclosure pertains to a cover for both magnetizing a tissue-penetrating medical device and providing a magnetic shielding to protect the magnetic charge on the device. A first embodiment pertains to a cover comprising a sleeve member having a hollow body, the hollow body having an exterior surface, an interior surface, a distal end and a proximal end to form a protective closure over a portion (e.g., a shaft) of a tissue-penetrating medical device, one or more magnets disposed along the sleeve member effective to magnetize a portion of a tissue-penetrating medical device, and a magnetic shield composed of one or more shielding materials that minimizes exposure of the clinical environment from magnetic fields generated from the one or more magnets disposed along the sleeve member and the magnetized portion of a tissue-penetrating medical device. In one or more embodiments, the sleeve member may have a length to cover the shaft of the tissue-penetrating medical device, and there are one or more magnets disposed inside the sleeve member. In one or more embodiments, the magnetic shield composed of one or more shielding materials surrounds the one or more magnets disposed inside the sleeve member. In one or more embodiments, the open end of the hollow tubular body provides a receiving space for receiving at least a portion (e.g., the shaft) of the tissue-penetrating medical device.

In one or more embodiments, the one or more magnets are fixed permanent magnets. In an alternate embodiment, the one or more magnets include a magnetic collar.

In one or more embodiments, the device-receiving space permits movement of the tissue-penetrating medical device into and out of the device-receiving space. In one or more embodiments, the device-receiving space permits movement of the tissue-penetrating medical device in a parallel direction to the longitudinal axis of the tissue-penetrating medical device.

According to one or more embodiments, the two or more magnets are disposed in slots positioned around the sleeve member. In one or more embodiments, the slots positioned around the sleeve member surround the device-receiving space. In one or more embodiments, the magnetic shield composed of one or more shielding materials surrounds a portion of the one or more magnets disposed inside the sleeve member. In one or more embodiments, the magnetic shield composed of one or more shielding materials surrounds the exterior surface of the sleeve member. In one or more embodiments, the a magnetic shield composed of one or more shielding materials surrounds the interior surface of the sleeve such that the one or more magnets disposed inside the sleeve member are exposed to the receiving space of the sleeve member.

In one embodiment, the shielding material may be a highly conductive material such as copper.

In another embodiment, the shielding material has a high magnetic permeability. The high magnetic permeability shielding material may be an alloy of nickel and iron metals. In a specific embodiment, the shielding material includes a ferromagnetic metal coating.

In yet another embodiment, the shielding material includes both a highly conductive material and a ferromagnetic metal coating. The highly conductive material may be copper and the high magnetic permeability shielding material may be an alloy of nickel and iron metals.

In one or more embodiments, the cover of the needle subassembly is in the form of a needle cover, catheter packaging or shipping container.

In one or more embodiments, the shielding material may be spray-coated onto an interior surface or exterior surface of the cover. In another embodiment, the shielding material may be spray-coated onto an interior surface and exterior surface of the cover.

In yet another embodiment, the magnetic shield composed of one or more shielding materials may be insert-molded into the cover.

In one or more embodiments, the tissue-penetrating medical device may be a needle, cannula, stylet, catheter, scalpel or guidewire. According to one more embodiments, the cover passively magnetizes the tissue-penetrating medical device upon removal of the tissue-penetrating medical device from the cover.

BRIEF DESCRIPTION OF THE DRAWINGS

FIG. 2A shows a perspective view of an embodiment of a needle cover having a magnetic shield of the present disclosure;

FIG. 2B shows a perspective view of an embodiment of a needle cover having a magnetic shield of the present disclosure;

FIG. 3A shows an embodiment of a tissue-penetrating medical device prior to insertion into a needle cover having a magnetic shield of the present disclosure;

FIG. 3B shows an embodiment of a tissue-penetrating medical device partially inserted into a needle cover having a magnetic shield of the present disclosure;

FIG. 3C shows an embodiment of a tissue-penetrating medical device fully inserted into a needle cover having a magnetic shield of the present disclosure;

FIG. 4 shows an embodiment of a tissue-penetrating medical device fully magnetized after being removed from a needle cover having a magnetic shield of the present disclosure;

FIG. 5 shows an embodiment of a tissue-penetrating medical device with a magnetic collar having a magnetic shield;

FIG. 7 shows an embodiment of a medical device with a cover having a magnetic shield of the present disclosure.

DETAILED DESCRIPTION

Figure 1:
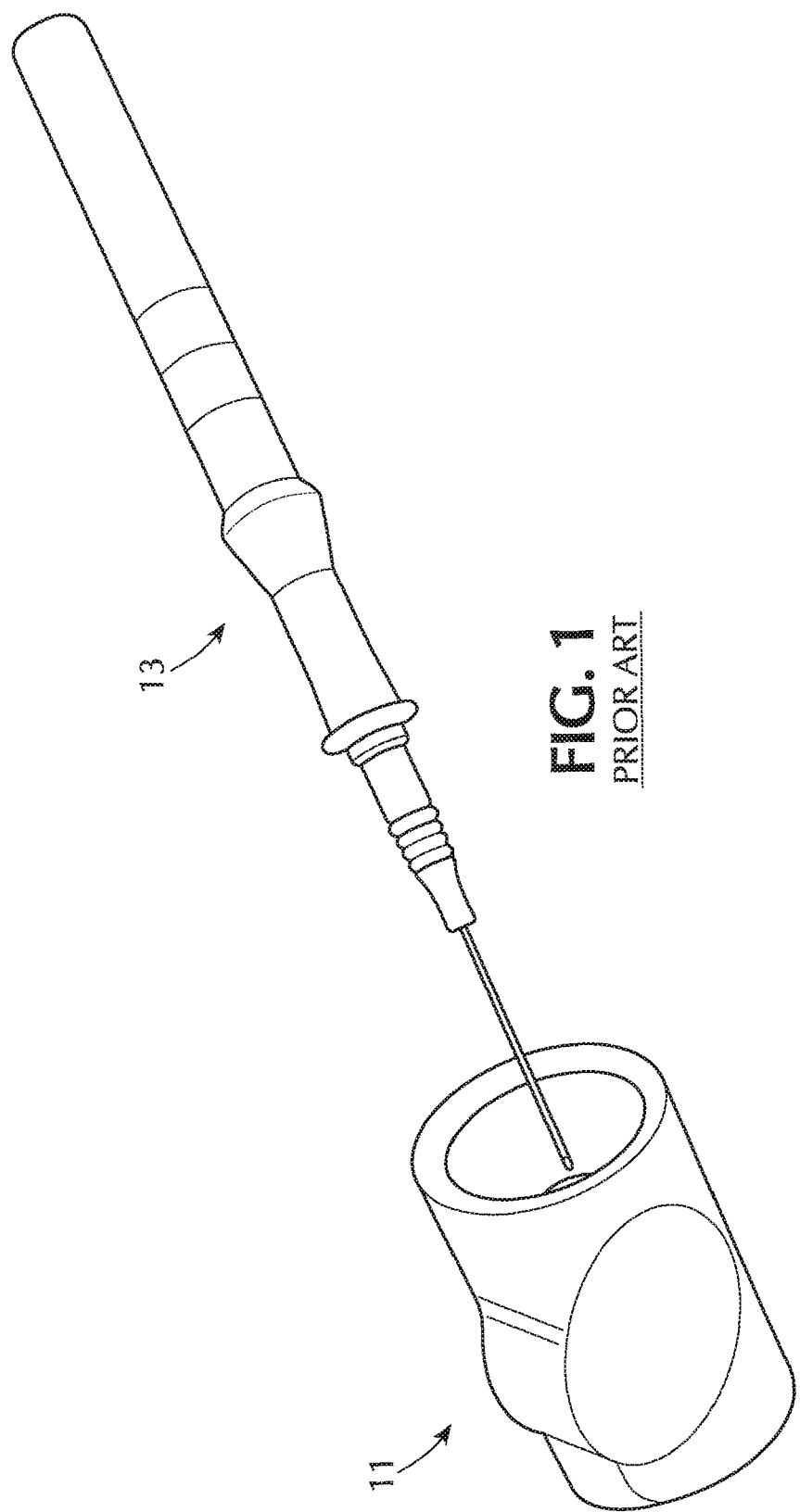
FIG. 1 shows a perspective view of a prior art disposable needle magnetizer.

Before describing several exemplary embodiments of the disclosure, it is to be understood that the description provided is not limited to the details of construction or process steps set forth in the following description. The devices and methods described herein are capable of other embodiments and of being practiced or being carried out in various ways.

In this disclosure, a convention is followed wherein the distal end of the device is the end closest to a patient and the proximal end of the device is the end away from the patient and closest to a practitioner.

Aspects of the disclosure pertain to a cover of a tissue-penetrating medical device with one or more magnets for passively magnetizing a portion of the tissue-penetrating medical device and a magnetic shield composed of one or more shielding materials associated with the cover that minimizes exposure of the clinical environment from magnetic fields generated from one or more magnets disposed within the cover and the magnetized portion of a tissue-penetrating medical device. The magnetic shield composed of one or more shielding materials also minimizes any adverse effects caused from exposure of the clinical environment to one or more permanent magnets disposed within the cover. Aspects of the disclosure pertain to an improved system that addresses the challenges to the existing technology and systems to passively magnetize an invasive medical device, such as a needle used with a peripheral intravenous (IV) catheter, while providing magnetic shielding to minimizing any effects to the clinical environment from magnetic fields generated within the cover from one or more permanent magnet disposed in the cover and the magnetized portion of the tissue-penetrating medical device.

One or more embodiments of the present disclosure relate to a cover for a tissue-penetrating medical device, the cover having an integrated magnet on or within the cover and a magnetic shield composed of one or more shielding materials associated with the cover that minimizes any adverse effects to the clinical environment from magnetic fields generated within the cover. According to one or more embodiments, the cover of the present disclosure passively and consistently magnetizes a portion (e.g., a shaft) of a tissue-penetrating medical device. In one or more embodiments, passive magnetization of the tissue-penetrating medical device is achieved with no additional or new clinical steps because the invasive medical device already includes a cover that covers the distal tip of the device. In one or more embodiments, the devices and systems described herein provide more precise control of the location of the magnet relative to the device to be magnetized, resulting in a more consistent and predictable magnetic field applied to the invasive medical device. In one or more embodiments, the devices and methods described herein create no additional risk of needle damage and pose no additional risk for contamination when compared to existing magnetizer devices.

Referring now to FIGS. 2A and 2B, one embodiment of a cover 12 of the present disclosure is shown for magnetizing a tissue-penetrating medical device 10, the cover 12 comprising a sleeve member 14 having a hollow body 20 having a distal end 21 and an open proximal end 22 to form a protective closure over a shaft 34 of a tissue-penetrating medical device 30, the cover having one or more magnets 50, and a magnetic shield 60 associated with the cover 12. In one or more embodiments, distal end 21 may be closed or open. In one or more embodiments, the magnetic shield 60 minimizes any effects to the clinical environment from magnetic fields generated within the cover from the one or more magnets disposed within the cover and/or from a magnetized portion of the tissue-penetrating medical device 10. In one or more embodiments, the magnetic shield 60 isolates the magnetized region of the tissue-penetrating medical device 50 from any external magnetic and electromagnetic fields thus keep the integrity of the magnetization of the magnetized region. In one or more embodiments, as shown in FIG. 5, the magnetic shield 60 contains the magnetic field generated by the magnetized region within the confines of the cover 12 to prevent the magnetized tissue-penetrating medical device 10 from causing magnetic interferences to sensitive equipment and devices in a hospital setting. The magnetic shield 60 would consist of one or more shielding material which would enclose the magnetized region.

In one or more embodiments, the hollow body 20 can be tubular or any other suitable shape. In the embodiment shown, the tissue-penetrating medical device 30 is shown as a needle assembly including a needle housing 32 and a shaft 34 of the needle having a sharp distal tip 36. It will be appreciated that in FIGS. 2A and 2B, the sleeve member 14 is shown as transparent and the shaft 34 of the tissue-penetrating medical device 30 is visible. The sleeve member 14 has a length L that covers the shaft 34 of the tissue-penetrating medical device 30, including the sharp distal tip 36 to prevent accidental needle sticks. The arrows shown in FIG. 2 with respect to the length "L" also show the longitudinal axis of the shaft 34. The open proximal end 22 of the hollow body 20 provides a device-receiving space 40 for receiving at least the shaft 34 of the tissue-penetrating medical device 30. The cover 12 includes at least one magnet 50, and in the embodiment show, at least two magnets 50 disposed on the sleeve member 14.

The device-receiving space 40 is sized and shaped to permit movement of the shaft 34 of the tissue-penetrating medical device 30 into and out of the device-receiving space 40. In one embodiment, the device-receiving space 40 permits movement of the shaft 34 of the tissue-penetrating medical device 30 into the device-receiving space 40 in a movement that is parallel to the longitudinal axis of the shaft 34 of tissue-penetrating medical device 30. One or more magnets 50 are disposed on the needle cover such that one face of the magnet is exposed to the interior of the receiving space 40 in order to magnetize a portion, e.g. shaft 34 of the tissue-penetrating medical device 30, while the opposite face of the magnet is exposed to the magnetic shield 60 associated with the cover 12 that prevents the magnetized portion, e.g. shaft 34, of the tissue-penetrating medical device from adversely affecting the clinical environment when the cover 12 is placed over the tissue-penetrating medical device 30. The cover 12 passively magnetizes the shaft 34 of the tissue-penetrating medical device 30 when the cover 12 is removed from the shaft 34 of the tissue-penetrating medical device thereby having a portion of shaft 34 being exposed to one or magnets 50 which are oriented to be exposed to the interior of the receiving space 40.

In one or more embodiments, tissue penetrating device 30 is not magnetized prior to placement of the tissue penetrating device into cover 12. When the tissue penetrating device 30 is placed into the device-receiving space 40 of cover 12, any distal section of the tissue penetrating device 30 that passes under the influences of the magnets 50 are magnetized. In one or more embodiments, portions of the tissue penetrating device 30 will be re-magnetized again when the cover 12 is removed prior to use and portions of the tissue penetrating device 30 pass under the one or more magnets 50 disposed within the device-receiving space 40 of cover 12, even if some section of tissue penetrating device 30 were de-magnetized due to storage or exposure to external magnetic fields while in storage.

According to one embodiment, the magnetic shield 60 composed of one or more shielding material may be spray-coated onto an exterior surface of the cover, as shown in FIG. 2A, or onto an interior surface of the cover, as shown in FIG. 2B, such that at least one face of magnet 50 is not coated with shielding material to allow the un-coated face of at least one magnet 50 to be exposed to a portion (e.g., a shaft 34) of a tissue-penetrating medical device when located in receiving space 40. In another embodiment, the magnetic shield 60 composed of one or more shielding material may be spray-coated onto an interior surface and exterior surface of the cover. In one or more embodiments, the magnetic shield 60 composed of one or more shielding material may be spray-coated onto an interior surface of the cover or an exterior surface of the cover to a thickness of $\frac{1}{1000}$th of an inch to 1 inch. The thickness of the magnetic shield may depend on the desired purpose or application of the medical device.

In another embodiment, the magnetic shield 60 composed of one or more shielding material may be insert-molded into the cover. Insert molding combines metal and thermoplastic materials, or multiple combinations of materials and components into a single unit. Insert molding processes typically involve an injection molding process in which solid pellets of raw material are melted and extruded into a mold—the plastic is then solidified—and then the press opens and the molded parts are ejected. The component to be insert-molded is placed in the mold, either by hand, or by automation before the material is injected into the mold. Then, as the material flows into features in the insert, the insert is anchored much more securely than if it were assembled to a previously molded component.

According to one or more embodiments, the cover 12 may be molded from a plastic having conductive additives or magnetic additives. In one embodiment, the cover 12 may be sterile and/or disposable.

In one or more embodiments, the shielding material may be a highly conductive material, such as copper or copper spray. A highly conductive shielding material will work in the presence of high frequency electromagnetic field. The varying magnetic field will generate eddy current within the conductor which would then cancel the magnetic field, preventing the magnetic field from reaching the magnetized region, thus preventing the potential demagnetization of the permanent magnets in the cover.

In one or more embodiments, the shielding material may have a high magnetic permeability. In one or more embodiments, the high magnetic permeability material may be iron, nickel, cobalt or an alloy or compounds containing one or more of these elements. In one or more embodiments, the high magnetic permeability material is comprised of an alloy of nickel and iron metals. The high magnetic permeability material may be Permalloy (a nickel-iron magnetic alloy, typically having about 80% nickel and about 15% iron and 5% molybdenum content) or ferromagnetic metal coating. In one or more embodiments, the shielding material may be composed of a nickel-iron alloy having approximately 77% nickel, 16% iron, 5% copper and 2% chromium or molybdenum. In yet another embodiment, the shielding material may be composed of approximately 80% nickel, 5% molybdenum, small amounts of various other elements such as silicon, and the remaining 12 to 15% iron. A high magnetic permeability shielding material will work well in the presence of static external magnetic fields. When an external static magnetic field is present near the magnetized region, the magnetic field line is drawn within the magnetic shield due to its high permeability, thus preventing the magnetic field from reaching the magnetized region, protecting the permanent magnets in the cover. Because the magnetic field generated by the permanent magnets in the cover and the magnetized needle are static, it is preferable to use shielding material with high magnetic permeability to prevent the magnetized tissue-penetrating medical device 10 from causing magnetic interferences to sensitive equipment and devices in a hospital setting.

If both a high frequency electromagnetic field and static external magnetic fields are expected to be present, the magnetic shield can consist of both highly conductive shielding material and high magnetic permeability material to block the external magnetic field from reaching the magnetized region. In a specific embodiment, the magnetic shield 60 includes a highly conductive material and a ferromagnetic metal coating. The highly conductive material may be copper.

FIGS. 3A to 3C show a medical device 100 including a tissue-penetrating medical device 130, a cover 112 for magnetizing the shaft 134 of the tissue-penetrating medical device 130. The cover 112 includes a sleeve member 114 having a hollow tubular body 120 having a distal end 121 and an open proximal end 122 to form a protective closure over the shaft 134 of the tissue-penetrating medical device 130, the sleeve member 114 having a length L to cover the shaft 134 of the tissue-penetrating medical device 130, the shaft 134 having a length L2 and a distal tip 136. The open end 122 of the hollow tubular body 120 provides a receiving space 140 for receiving at least the shaft 134 of the tissue-penetrating medical device 130. Cover 112 includes two magnets 150 and a magnetic shield 160 that minimizes any effects to the clinical environment from magnetic fields generated from the two magnets 150 within the cover. It will be understood that while two magnets 150 are shown, the device is not limited to a particular number of magnets or to a particular location of the magnets around the sleeve member. Magnets 150 may be positioned in any position or orientation around the sleeve member. In one or more embodiments, a single magnet can be utilized to magnetize the shaft 134, or more than two magnets can be utilized. Magnetic shield 160 composed of one or more shielding materials may be spray-coated onto an interior surface of the cover 112 or an exterior surface of the cover 112 such that at least one face of magnet 150 is not coated with shielding material to allow the un-coated face of at least one magnet 150 to be exposed to a portion (e.g., a shaft 134) of a tissue-penetrating medical device 130 when located in receiving space 140. In one or more embodiments, the magnetic shield 160 composed of one or more shielding materials may be spray-coated onto an interior surface of the cover or an exterior surface of the cover to a thickness of 1/1000th of an inch to 1 inch. The thickness of the magnetic shield 160 composed of one or more shielding materials may depend on the desired purpose or application of the medical device. In another embodiment, the magnetic shield 160 may be insert-molded into the cover.

In embodiments in which two magnets are utilized, the orientation of the magnetic fields of the two magnets can vary. One magnet can have north and south poles on axis with shaft of the tissue-penetrating medical device, while the second magnet can have north and south poles off-axis or perpendicular to the shaft of the tissue-penetrating medical device. Alternatively, the two magnets both can have north and south poles off axis with the shaft of the tissue-penetrating medical device, or the two magnets both can have north and south poles on axis with the shaft of the tissue-penetrating medical device.

FIG. 3A shows the tissue-penetrating medical device 130 prior to insertion into the cover 112 of the present disclosure. The tissue penetrating medical device 130 includes the shaft 134 having a length L2, a distal tip 136, and the shaft 134 is mounted to the housing 130 by a hub 152. In one or more embodiments, the hub 152 includes a hub magnet 155. In one or more embodiments, hub magnet 155 is a permanent fixed magnet. Hub magnet 155 may provide for a fixed magnetic reference point when the tissue-penetrating needle is used with a combination of ultrasound and magnetic technologies to provide visualization of subdermal anatomy and device position. FIG. 3B shows the shaft 134 of the tissue-penetrating medical device 130 partially inserted into a cover 112 of the present disclosure. FIG. 3C shows the shaft 134 of the tissue-penetrating medical 30 device fully inserted into a cover 112 of the present disclosure. The medical device 100 as shown in FIG. 3C can be packaged and ready for use for a medical procedure. The medical device 100 shown in FIG. 3C can be packaged together with other devices as part of a larger medical device assembly. Thus, FIG. 3C shows a medical device 100 which is a needle subassembly having a cover 112 having at least one magnet 150 configured to magnetize shaft 134 of the medical device 100 upon removal of the cover 112 from the shaft. The medical device 100 could further be packaged as part of a catheter assembly including a catheter adapter subassembly.

Depending on the magnetized region of the medial device, the magnetic shield may be in the form of or incorporated into a needle cover, individual catheter wrapper, catheter dispenser, product packaging or a catheter shipper.

When the magnetic shield is incorporated into individual medical device packaging, the entire packaging can be coated with the magnetic shielding material. Alternatively, only the sections of the packaging enclosing the magnetized regions may contains the magnetic shielding material. Such approach would facilitate ease of sterilization through the packaging.

FIG. 4 shows an embodiment with a magnetized needle ready for insertion after cover 112 has been removed. This allows the device to be used with the procedural guidance systems that utilize magnetic sensors as a means of measuring and predicting needle tip location relative to the target anatomy.

As shown in FIG. 4, the tissue-penetrating medical device 130 with the shaft 134 magnetized after the shaft 134 has been removed from the needle cover shown in FIGS. 3B-3C. As shown in FIGS. 3B-3C, two magnets 150 can be integrated into cover 112 so that the cover 112 passively magnetizes the shaft 134 upon removal of cover 112. The embodiment shown in FIGS. 3B-3C shows two magnets 150 positioned around cover 112. Such a cover could be easily integrated in existing catheter assemblies and other invasive medical devices such as guidewires and stylets to enable the magnetization of the shafts of various invasive medical devices upon removal of the cover to passively magnetize the shaft. The axial position of the magnets can be modified and positioned relative to the shaft length and the desired portion of the shaft to be magnetized. For example, in the case of a needle, the magnets can be specifically positioned based on the gauge and length of the needle. As shown in FIG. 3B, the positioning of the magnets would result in the shaft 134 being magnetized from the approximately the position P shown in FIG. 3C to the distal tip 136 of the shaft 134 as the portion of the shaft from P to the distal tip will be moved through the magnetic field provided by the magnets 150. This the tissue-penetrating medical device 130 can now be used with a procedural guidance system that utilize magnetic sensors as a means of measuring and predicting needle tip location relative to the target anatomy. In one or more embodiments, the distal end of the tissue penetrating medical device 130 includes a notch 137 located on the distal tip 136 of the shaft 134 to provide immediate confirmation of vessel entry at a point of insertion. In one or more embodiments, the magnetized portion of the tissue-penetrating medical device may comprise a partial length of the tissue-penetrating medical device. In one or more embodiments, the magnetized portion of the tissue-penetrating medical device may comprise a distal tip of the tissue-penetrating medical device. In one or more embodiments, the magnetized portion of the tissue-penetrating medical device may comprise an entire length of the tissue-penetrating medical device.

FIG. 5 shows an embodiment of a tissue-penetrating medical device 230 including a cover 212 having a magnetizing collar 260, which can be a magnet in the shape of the collar 260 as shown. Magnetic shield 265 composed of one or more shielding materials may be spray-coated onto an exterior surface 261 of the collar 260 such that the interior surface 262 is not coated with shielding material to allow the un-coated interior surface to be exposed to a portion (e.g., a shaft 234) of a tissue-penetrating medical device 230 is located in receiving space 240. In one or more embodiments, the magnetic shield 265 composed of one or more shielding materials may be spray-coated onto exterior surface 261 of the collar 260 to a thickness of ¹⁄₁₀₀₀th of an inch to 1 inch. The thickness of the magnetic shield 265 may depend on the desired purpose or application of the medical device. The cover 212 includes a sleeve member 214 having a hollow tubular body 220 having a distal end 221 and a proximal end 222 to form a protective closure over the shaft 234 of the tissue-penetrating medical device 230. The open end 222 of the hollow tubular body 220 provides a receiving space 240 for receiving at least the shaft 234 of the tissue-penetrating medical device 230. The magnetizing collar 260 is show as being disconnected from the cover 212, but the magnetizing collar 260 is variably positioned along the length L3 of the cover 212 relative to the shaft 234. The magnetizing collar 260 can be used as a single use disposable item, or the magnetizing collar 260 may be reusable since the needle cover stays in place during the magnetization step. Therefore, according to one or more embodiments, the magnetizing collar 260 is detachably mounted to the cover 212. In alternative embodiments, the magnetizing collar 260 is permanently mounted to the cover 260. The magnetizing collar 260 can be slidably moved along the length of the cover 212. In other embodiments, the length L4 of the magnetizing collar 260 may be equal to the length L3 of the cover 212 such that the entire shaft 234 of the tissue-penetrating medical device 230. In other embodiments, the length L4 of the magnetizing collar 260 is 10%, 20%, 30%, 40%, 50%, 60%, 70%, 80% or 90% of the length L3 of the cover 212. The magnetizing collar 260 can be a tubular magnet that substantially surrounds the periphery of the cover, or the magnetizing collar 260 can be a cover made of plastic or other material with an array of magnets substantially surrounding the periphery of the cover.

Figure 6B:
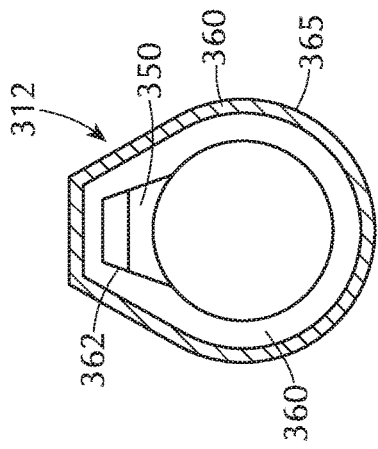
FIG. 6B shows an end view of a needle cover with one embedded magnet and a magnetic shield of the present disclosure.
Figure 6C:
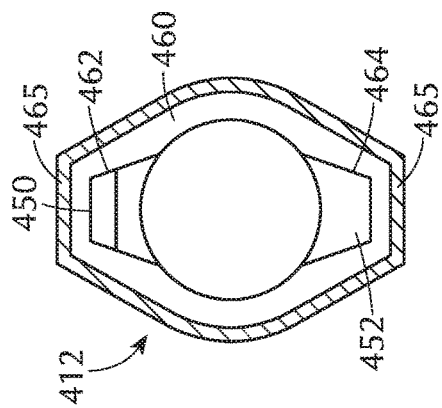
FIG. 6C shows an end view of a needle cover with two embedded magnets and a magnetic shield of the present disclosure.
Figure 6A:
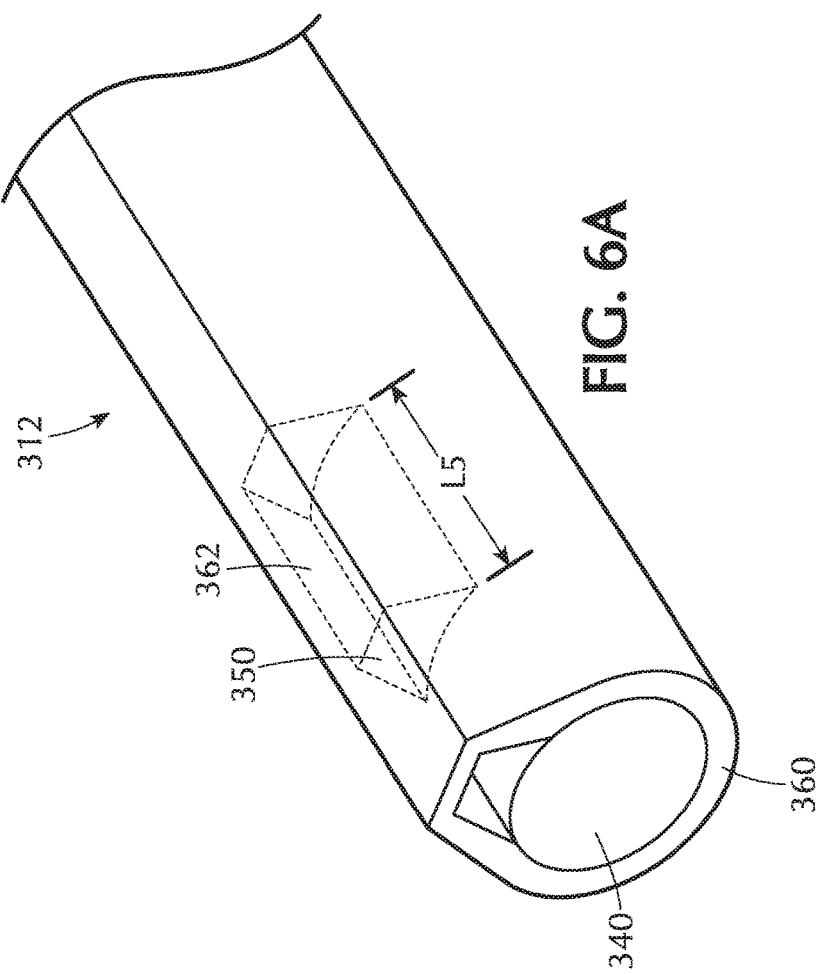
FIG. 6A shows a partial perspective view of a tip of a needle cover with an embedded magnet and a magnetic shield of the present disclosure.

FIGS. 6A-6C show one way of integrating at least one magnet with a cover for a tissue-penetrating medical device. According to one or more embodiments, as shown in FIG. 6A the cover 312 may have a wall 360 made entirely of a magnetic shielding material wherein one or more magnets 350 are disposed in slots 362 positioned on the interior surface of the receiving space 340 around the sleeve member. In one or more embodiments, the slots 362 are positioned around the sleeve member surround the device-receiving space 340. In one or more embodiments, the magnetic shield composed of one or more shielding material surrounds a portion of the one or more magnets disposed inside the sleeve member. In one or more embodiments, the magnetic shield composed of one or more shielding material surrounds the exterior surface of the sleeve member. In one or more embodiments, the magnetic shield composed of one or more shielding material surrounds the interior surface of the sleeve such that the one or more magnets disposed inside the sleeve member are exposed to the receiving space of the sleeve member.

FIG. 6A shows a partial perspective view and FIG. 6B shows an end view of a cover 312 having an embedded magnetic 350 in the wall 360 of the cover 360 having a magnetic shield 365 comprised of magnetic material along the exterior surface of wall 360. The magnet 350 is embedded in a slot 362. The magnet 350 can be sized to be slidably mounted within the slot 362 and held in place by friction fit, or the magnet can be attached with an adhesive or other suitable ways. Alternatively, the magnet 350 could be integrally molded into the wall 360 during the forming process for the cover 312. The length L5 of the magnet 350 shown in FIG. 6A is shown as being less than the length of the cover. According to one or more embodiments, the length L5 of the magnet 350 can be equal to the length of the cover, or 10%, 20%, 30%, 40%, 50%, 60%, 70%, 80% or 90% of the length of the cover.

FIG. 6C shows an embodiment of a cover 412 with a first magnet 450 in a first slot 462 of the wall 460 of the cover 412, and a second magnet 452 in a second slot 464 in the wall 460 of the cover. The first magnet 450 and second magnet 452 are shown as being positioned around the cover 412, for example, 180 degrees from each other. It will be understood that the two magnets can be in other positions with respect to each other. Additionally, the cover 412 can include more than two magnets. The first magnet 450 and second magnet 452 can be slidably mounted in the respective first slot 462 and the second slot 464 and held in place by friction fit, or they could be held in place by adhesive. In alternative embodiments, the magnets can be integrally molded with the cover 412. The two or more magnets may have oppositely oriented poles. As an exemplary embodiment, magnetic shield 465 is shown comprised of magnetic material along the interior surface of first slot 462 and the second slot 464.

In alternative embodiments, a needle cover is provided that has geometric dimensions that permit the needle cover to be placed inside existing needle magnetizing devices while the needle cover is covering the shaft of the needle. The distal end of the needle cover may be used to limit the depth of insertion by providing a stop to contact the bottom of the needle magnetizing device. Alternatively, a feature near the proximal portion of the needle cover can be provided on the cover to limit the depth of insertion by a stop on the proximal opening of the needle magnetizer.

The covers described herein can have a variety of properties. In one or more embodiments, the covers are formed from plastic. In one or more embodiments, the covers are sterile. In one or more embodiments, the covers are disposable. In other embodiments, the covers may be both sterile and disposable.

The tissue-penetrating medical device may be a needle, catheter, introducer needle, stylet, scalpel or guidewire. In one embodiment, the tissue-penetrating medical device is a needle, which when magnetized can be used with a procedural guidance system to locate and project the position of the needle during an invasive medical procedure. The tissue-penetrating medical device according to one or more embodiments is includes a magnetizable metallic material. In a specific embodiment, the magnetizable metallic material is magnetizable stainless steel.

The covers described herein may also be incorporated into a vascular access device comprising a catheter, a catheter adapter subassembly, and a needle subassembly including an introducer needle, a needle hub connected to the proximal end of the introducer needle and a needle cover according to any of the embodiments described herein. The needle cover may include a plastic sleeve member having a hollow tubular body to form a protective closure over the introducer needle, and two or more magnets disposed on the needle cover as described herein.

Figure 8:
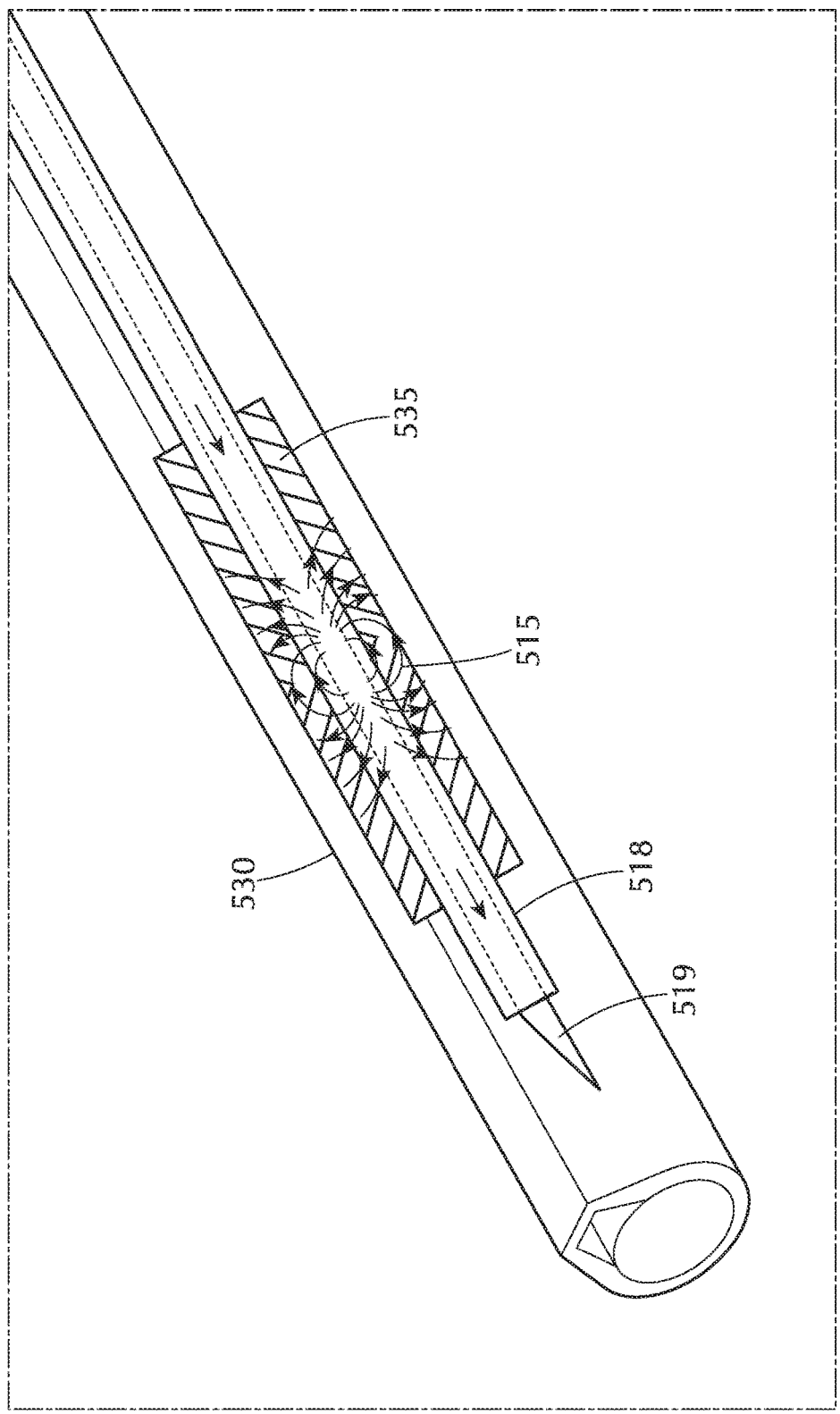
FIG. 8 shows a partial exploded view of the embodiment of a medical device shown in FIG. 7 having a magnetic field contained within the cover having a magnetic shield.

An example of a medical device assembly, specifically a vascular access device including a catheter according to any of the foregoing embodiments described above is illustrated in FIG. 7. The medical device assembly 500 shown in FIG. 7 comprises a tissue penetrating medical device in the form of a needle subassembly 514, and a catheter adapter subassembly 512 including a catheter adapter body 516 and a catheter tubing 518 and a permanent magnet element 532, a cover 530 having an embedded magnetic 535 in the wall of the cover 530 having a magnetic shield 565 comprised of magnetic material along the exterior surface of wall. FIG. 8 shows a partial exploded view of the embodiment of a medical device shown in FIG. 7 having a magnetic field 515 contained within the cover having a magnetic shield 530. In one or more embodiments, the catheter adapter is connected to the proximal end of the shaft.

A permanent magnet element located along the introducer needle may serve as an additional reference point when used in combination with ultrasound and magnetic technologies to provide visualization of subdermal anatomy and device position. A needle 519 within the catheter tubing 518 shows a cover 530, and the needle has been magnetized upon removal of a cap including a magnet as described with respect to FIGS. 2-7 herein. Magnetizing the needle with the cover as described herein creates a magnetic field in the magnetic region.

The medical device 500 may be a vascular access device which includes a lateral access port 556 and may be connected to a section of an extension tube 560 for establishing fluid communication between an IV fluid source and the catheter tubing 518. In one or more embodiments, the extension tube 560 is built-in to reduce contamination and mechanical phlebitis by eliminating manipulation at the insertion site. In one or more embodiments, the extension tube 560 is compatible with high pressure injection. In one or more embodiments, the extension tube 560 provides continuous confirmation of vessel access during advancement of the catheter into the patient vein.

In one or more embodiments, a needle of a needle subassembly 514 is inserted into a lumen of the catheter tubing 518. The needle subassembly 514 is shown as including finger grips 584 positioned at the sides of the needle subassembly 514 to facilitate various insertion techniques. In one or more embodiments, bumps may be present on the finger grip to indicate where to the user may grip the device for needle removal. In one or more embodiments, a thumb pad 585, having a gently convex surface, is provided at the proximal end of the needle subassembly 514. A flange 586, having a gently convex surface, is provided at the proximal end of the needle subassembly 514 to provide a finger pad. A wing member 570, thumb pad 585 and flange 586 may be utilized by the user during insertion, permitting the user to elect which insertion technique to employ.

In one or more embodiments, the needle subassembly 514 includes a needle shield 580. The needle shield 580 may be a design adapted to secure the tip of the needle within the shield after use. In one or more embodiments, the needle shield 580 may be activated passively. The needle tip is completely covered by the needle shield 580 in a fixed position. In one or more embodiments, a ferrule, crimp or other structure may be included near the tip for engagement with a needle shield in certain applications.

A push tab 581 may be provided to facilitate catheter advancement during insertion. The push tab 581 also allows for one-handed or two-handed advancement. In one or more embodiments, the push tab 581 is removed with the needle shield 580. A clamp 582 may also be included on the extension tubing to prevent blood flow when replacing the access port.

In one or more embodiments, the vascular access device 500 further includes a first luer access 572 and a second luer access 573 in fluid communication with the extension tube 560, a blood control split septum 574 associated with the first luer access 572, and an air vent 576 associated with the second luer access 573. Split septum 574 allows for a reduction in catheter-related bloodstream infection (CRBSI) while providing unrestricted flow and a straight fluid path and functions as a blood control septum. In one or more embodiments, the split septum 574 may be located in an internal cavity of the catheter adapter or on the distal end of the catheter adapter. In yet another embodiment, the split septum 574 may be located on a distal end of the extension tube 560. The air vent 576 allows air to escape from the system during insertion, providing continuous confirmation of vascular access while preventing leakage of blood from the system during insertion. In one or more embodiments, the air vent 576 may be at the distal end of extension tube 560.

In one or more embodiments, the base unit can be integrated into the ultrasound system with the ultrasound processor and a magnetometric detector being in direct communication with the ultrasound system either via wireless link or using the same physical cable.

Another aspect of the disclosure pertains to a method of magnetizing a tissue-penetrating medical device. Embodiments of the method include positioning a shaft of the tissue-penetrating medical device into a cover having a device-receiving space, at least one magnet disposed within the device-receiving space, and a magnetic shield composed of one or more shielding materials associated with the cover; and subsequently removing the tissue-penetrating medical device from the device-receiving space to magnetize the shaft of the tissue-penetrating medical device.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cover for magnetizing a tissue-penetrating medical device comprising:
   a sleeve member having a hollow body with an exterior surface, an interior surface, a proximal end, and a distal end to form a protective closure over a shaft of a tissue-penetrating medical device having a longitudinal axis, the proximal end of the hollow body providing a receiving space for receiving at least a shaft of the tissue-penetrating medical device;
   one or more magnets disposed along the sleeve member effective to magnetize the shaft; and
   a magnetic shield composed of one or more shielding materials spray-coated onto the interior surface of the sleeve member, a first face of the one or more magnets being exposed to the receiving space and an opposite face of the one of one or more magnets being exposed to the interior surface of the sleeve with the spray-coated magnetic shield.

2. The cover of claim 1, wherein the receiving space permits movement of the shaft of the tissue-penetrating medical device in the receiving space in a direction parallel to the longitudinal axis of the tissue-penetrating medical device.

3. The cover of claim 1, wherein the receiving space permits movement of the shaft of the tissue-penetrating medical device into and out of the receiving space.

4. The cover of claim 1, wherein the two or more magnets are disposed along the interior surface of sleeve member.

5. The cover of claim 1, wherein the one or more shielding material is a highly conductive material.

6. The cover of claim 5, wherein the one or more shielding material comprises copper.

7. The cover of claim 1, wherein the one or more shielding material has a high magnetic permeability.

8. The cover of claim 7, wherein the one or more shielding material comprises an alloy of nickel and iron metals.

9. The cover of claim 8, wherein the one or more shielding material includes a ferromagnetic metal coating.

10. The cover of claim 1, wherein the one or more shielding material includes a highly conductive material and includes a ferromagnetic metal coating.

11. The cover of claim 10, wherein the highly conductive material comprises copper.

12. The cover of claim 1, wherein the cover is selected from a needle cover, catheter packaging or a shipping container.

13. The cover of claim 1, wherein the one or more shielding material is spray-coated onto an exterior surface of the cover.

14. The cover of claim 1, wherein the tissue-penetrating medical device is a needle assembly, a stylet, catheter, introducer needle, scalpel or guidewire.

15. The cover of claim 1, wherein the one or more magnets comprises a fixed permanent magnet.

16. The cover of claim 1, wherein the one or more magnets comprises a magnetic collar, the magnetic collar surrounding the cover.

17. The cover of claim 16, wherein the magnetic collar is moveable along the shaft.

18. The cover of claim 1, wherein the shielding material may be insert-molded into the cover.

19. The cover of claim 1, wherein the shaft of the tissue-penetrating medical device comprises a magnetizable metallic material.

20. The cover of claim 1, wherein the shielding material is spray-coated to a thickness of $1/1000$th of an inch to 1 inch.

* * * * *